United States Patent [19]

Kozak, Jr. et al.

[11] 4,280,000

[45] Jul. 21, 1981

[54] METHOD FOR OBTAINING MOLD SPORE MATERIAL

[75] Inventors: Peter P. Kozak, Jr., Santa Ana; Janet M. Gallup, Garden Grove, both of Calif.

[73] Assignees: Cummins, Kozak and Gillman; Janet Gallup, both of Orange, Calif. ; part interest to each

[21] Appl. No.: 110,203

[22] Filed: Jan. 7, 1980

[51] Int. Cl.³ .............................................. C12N 3/00
[52] U.S. Cl. .................................. 435/242; 435/254; 435/299
[58] Field of Search ................ 435/242, 254, 292, 299

[56] References Cited

U.S. PATENT DOCUMENTS

| | | | |
|---|---|---|---|
| 3,294,647 | 12/1966 | Sehgal et al. | 435/242 |
| 3,300,390 | 1/1967 | Tiner et al. | 435/242 |
| 3,357,895 | 12/1967 | Cherry | 435/242 |
| 3,616,246 | 10/1971 | Cherry | 435/242 |
| 4,046,593 | 9/1977 | Au et al. | 435/242 |

*Primary Examiner*—R. B. Penland
*Attorney, Agent, or Firm*—Gordon L. Peterson

[57] ABSTRACT

A method of obtaining mold spore material useful for inhalant allergy comprising growing a mold which includes mold spores and mycelia on a medium which supports growth of the mold. A porous barrier is provided between the medium and at least some of the mold so that a first group of the mold spores and mycelia lies on the side of the barrier remote from the medium and a second group of mycelia lies in the medium and on the other side of the barrier. After optimum growth of the mold has occurred, the barrier and the first group of mold spores and mycelia are removed from the medium and allowed to dry. Subsequently, at least some of the first group of mold spores and mycelia are removed from the barrier so that the step of removing separate the first group of mold spores and mycelia from the second group of mycelia. Following drying, the removed mold spores and mycelia are sieved to separate the mold spores from most of the mycelia.

13 Claims, 5 Drawing Figures

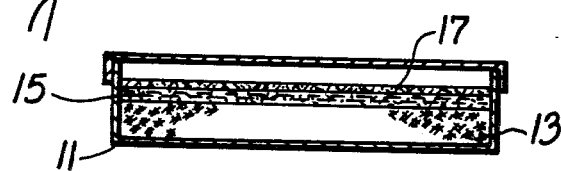
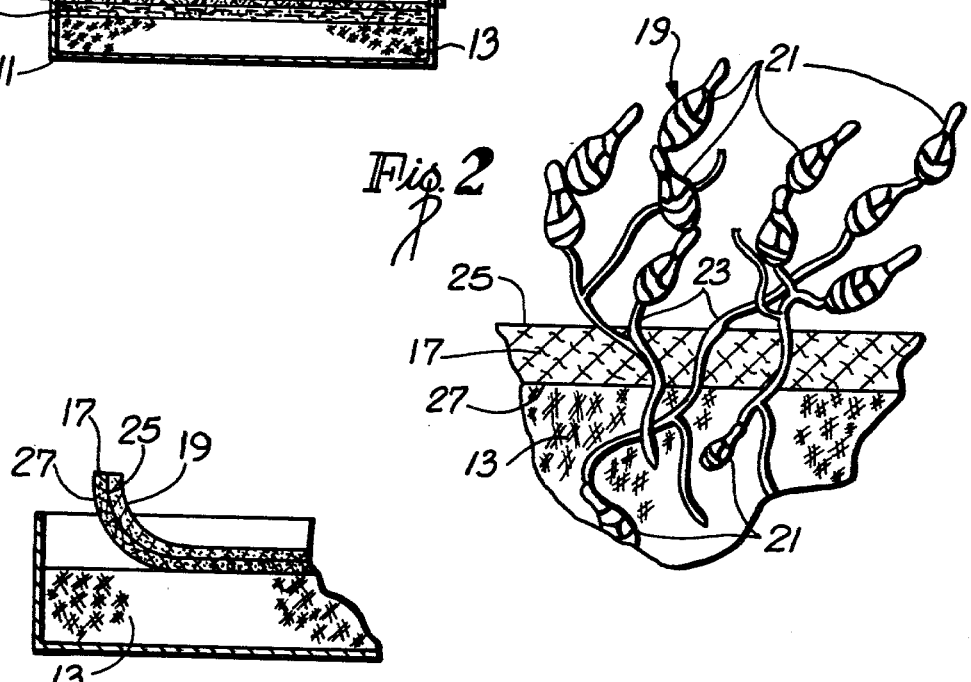
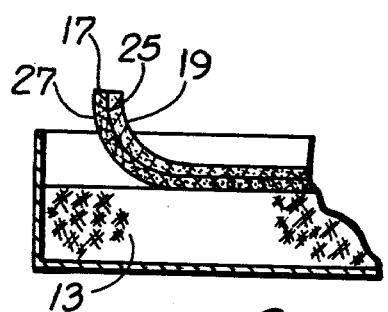
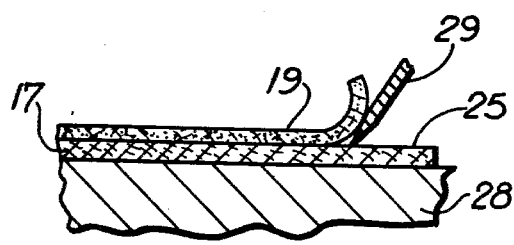
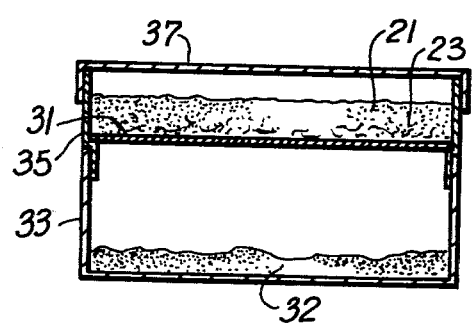

METHOD FOR OBTAINING MOLD SPORE MATERIAL

BACKGROUND OF THE INVENTION

The air we breathe contains various different kinds of mold spores. Unfortunately, many people are allergic to one or more of these mold spores.

In the treatment of mold spore allergy, an extract is prepared from the mold to which the patient exhibits allergic tendencies. This extract is injected into the patient at intervals, with the dosage being progressively increased over a period of time. The same, or a similar extract, can be used for the standard skin test to determine a patient's allergic tendencies with respect to a particular mold.

Unfortunately, even after three or four years of injection treatment, it is rare to observe any reduction in skin test reactivity to mold extracts. Immunotherapy with pollen and bee venom, by contrast, will generally result in reduction of symptoms on re-exposure to the antigen, a decrease in skin test reactivity and/or changes in other in vitro tests.

A primary problem with prior art mold extracts is that they are made from mold spore material which is not believed to have adequate concentrations of spore material. It is also believed that the composition and purity of a given mold extract is not constant from batch to batch. These factors materially reduce the effectiveness of the usual injection treatment for inhalant mold allergy.

Molds of the type relevant to inhalant mold allergy comprise mold spores and mycelia. The mold spore is the material to which patients are commonly allergic, and the mycelia is the growing structure for the mold spores. Mold spores are somewhat analogous to the fruit of a tree, and mycelia is analogous to the branches and root structure.

Because only the mold spore is the allergen, in preparing mold spore material from which a mold extract is to be made, it is first necessary to separate the mold spores from the mycelia. This is roughly analogous to harvesting the leaves on a tree by severing the fruit from the branches of the tree. However, the job of mold-spore harvesting is infinitely more difficult than leaf harvesting because the mold spores are of microscopic size and cannot be hand picked as in the case of the usual agricultural harvesting methods.

Various methods are known for obtaining a mold spore material for use in making a mold extract. For example, mold spores can be seeded onto a solid medium, allowed to grow and then brushed from the medium. Also, mold spores can be grown on cellophane which is placed on the surface of a growth-supporting medium. After a sufficient growth has been attained, the cellophane is folded together, lifted from the medium, dried with moderate heat and then subjected to the usual extracting methods. None of these prior art methods provides an extract of the desired purity nor an extract of adequately repeatable composition.

SUMMARY OF THE INVENTION

This invention provides a method of obtaining substantially pure mold spore material which has increased purity which may average from 90 to 95 percent. In addition, this degree of purity is repeatable from batch to batch. Purity is determined by placing the mold spore material in suspension and determining the ratio of mold spores to mycelia fragments under a microscope in a cell counting chamber. A purity of 90 to 95 percent means that there are 90 to 95 mold spores to five to ten mycelia fragments in the suspension.

Another advantage of this invention is that the mold spores can be harvested and a mold extract prepared without damaging them structurally as can occur with certain prior art processes where the harvesting involves pulverization of the mold material. Also, the preparation of the extract utilizing the mold spores does not alter or break open the mold spores as is required in some prior art defatting steps.

The method of this invention is applicable to virtually any mold which includes mold spores and mycelia. As such, the method of this invention is applicable to those molds recognized in inhalant allergy. For example, this invention is applicable to the growing and harvesting of Alternaria, Cladosporium, Penicillium, Aspergillus, Drechslera and Epicoccum.

In order to grow a mold, a medium must be utilized to support growth of the mold. Virtually any medium which will support growth of the mold and promote good sporulation may be utilized.

By appropriately growing the mold, certain advantages are obtained when harvesting the mold spores. Specifically, advantages are obtained by providing a porous barrier between the medium and at least some of the mold being grown. This results in a first group of mold spores and mycelia lying on the side of the barrier remote from the medium and a second group of mycelia and a few mold spores lying within the medium and/or between the medium and the other side of the barrier. For example, the porous barrier can be placed on the medium and the mold planted on the side of the barrier remote from the medium. Alternatively, the mold can first be planted on the upper surface of the medium and thereafter the barrier can be placed on the planted mold. It is easier to plant the mold directly on the surface of the medium, and this may also enhance mold growth as the mold is in direct contact with the medium.

Regardless of which planting technique is used, the mold grows through the barrier because the barrier is sufficiently porous to permit this. The barrier, which may be in the form of a flexible porous sheet, separates the first group of spores and mycelia from the medium.

After maximum mold growth has been attained, the barrier is removed from the medium, together with the first group of mold spores and mycelia. This leaves some of the mycelia within the medium, and some medium and spores may be removed with the barrier and lie on the opposite side of the barrier from the first group of mold spores and mycelia. Because the barrier separates the first group of mold spores and mycelia from the medium, removal of the barrier prevents any of the medium from getting into the first group of mold spores and mycelia. The separation of the medium from the first group of spores and mycelia permits the use of media which would not otherwise be usable because of its tendency to contaminate the mold.

The barrier is preferably peeled off gently from the medium to avoid taking much, if any, of the medium along with the barrier. The barrier with the mold spores and mycelia thereon is then dried at ambient temperature for a suitable period, such as four to ten days. Thereafter, the first group of mold spores and mycelia is scraped gently from the barrier using a minimum of pressure to avoid scraping off any of the barrier. The scraped material includes mold spores, mycelia and possibly some fibers or fragments of the barrier. Although some mycelia is included with the scraped material, most of the mycelia is left in or on the medium and on the other side of the barrier.

The removed material is then air-dried at ambient temperature for a suitable period, such as two to four days. Thereafter, the material is sieved. Although the material can be sieved multiple times, to increase the yield of spore material, it is preferred to sieve it only once. The mold spores tend to pass through the sieve and the mycelia and other impurities, if any, do not pass through the sieve. Following the sieving process, the resulting mold spore material may have a purity of from 90 to 95 percent.

The mold spores of the mold spore material are intact and are not broken open or pulverized. Consequently, surface antigens of the mold spores can be extracted. It is desired to extract only the surface antigens, and if the spores are broken open, antigens from the spore interior are also included in the extract. A preferred method of extracting the surface antigens includes mixing a known amount of the mold spore material with a known amount of extraction liquid and maintaining the mixture at a temperature below ambient.

The invention, together with further features and advantages thereof, may best be understood by reference to the following description taken in connection with the accompanying illustrative drawing.

BRIEF DESCRIPTION OF THE DRAWING

FIG. 1 is a schematic sectional view illustrating the medium, the porous barrier and the mold in a sterile petri dish just after planting of the mold.

FIG. 2 is an enlarged fragmentary sectional view illustrating a mold colony and portions of the porous barrier and medium.

FIG. 3 is a sectional view similar to FIG. 1 illustrating how the barrier and mold can be peeled off of the media.

FIG. 4 is an elevational view illustrating one way of removing the mold spores and mycelia from the porous barrier.

FIG. 5 is a sectional view illustrating sieving of the removed mold spores and mycelia.

DESCRIPTION OF THE PREFERRED EMBODIMENT

FIG. 1 illustrates a container 11 in the form of a sterile petri dish having a removable sterile cover 12 and containing a medium 13 for supporting mold growth, a mold suspension 15 spread evenly over the upper surface of the medium, and a barrier in the form of a flexible, porous sheet 17 overlying the mold suspension. The container 11 may be any kind which is suitable for containing the medium 13, but to avoid contaminating the mold, it is important that the container 11 be sterile and covered with the sterile cover 12. In fact, the entire process is carried out under sterile conditions.

The medium 13 can be any medium suitable for supporting growth and heavy sporulation of the mold which it is desired to grow and it may be in the form of a gelatin-like mass. Many different kinds of media for growing various different kinds of molds are known. For example, Sabouraud's medium is a common medium for growing molds, such as Alternaria. Various different kinds of media are commercially available, such as Murashige and Skoog Agar from Flow Labs of 936 West Hyde Park Blvd., Inglewood, Calif., or Potato Dextrose Agar from Difco Labs of Detroit, Mich. Special media mixes can also be prepared, such as Sabouraud's medium mixed with carboxymethylcellulose and Fusarium sporulation agar.

The mold can be planted on the medium 13 in various different ways. The preferred method is to first grow the desired mold on a plate using known techniques and, when the mold is in a heavily sporulating growth stage, swab the plate to remove the spores. A suspension is then made from the spores using sterile water, and the suspension is applied to the upper surface of the medium 13 using a pipette and a stirring stick or other suitable implement to spread the suspension evenly over the upper surface of the medium.

Immediately after placing the suspension 15 on the medium 13, the sheet 17, which has been previously sterilized, is placed over the suspension 15. It has been found that application of the sheet 17 twenty-four hours after application of the mold suspension 15 delays spore formation. For this reason, it is preferred to apply the sheet 17 soon after applying the suspension 15.

The sheet 17 should be porous to facilitate growth of the mold through it. It should also be strong enough to be peeled off of the medium 13 after suitable mold growth has taken place. The sheet 17 should also be very thin. Although various different materials may be used for the sheet 17, filter paper is preferred. Filter paper No. 42 and No. 54 sold by Whatman Inc. of 9 Bridewell Place, Clifton, N.J. are preferred as they enable good growth of the mold and they were sufficiently strong to be easily peeled from the medium 13. Glass fiber filter paper and a polyethylene sheet has also been used. However, the polyethylene sheet was too thick, and no significant mold growth occurred. The glass fiber filter paper supported good mold growth, but it was not strong enough to be easily removed from the associated medium. For example, filter paper Nos. 42 and 54 have thicknesses of about 0.20 and 0.18 mm., respectively.

Alternatively, the sheet 17 may be first placed on the upper surface of the medium 13 and the suspension 15 spread over the upper surface of the sheet. In this event, the sheet 17 is sandwiched between the suspension 15 and the medium 13.

After the mold is planted or innoculated, it is allowed to grow until optimum growth and sporulation have occurred. The mold should ordinarily be allowed to grow from about two to five weeks depending on the type of mold, the lighting and other growing conditions.

FIG. 2 shows mold colony 19 which comprises mold spores 21 and mycelia 23. The sheet 17 has an outer face 25 and an inner face 27. During the mold-growing process, the mold grows through the porous sheet 17 so that most, or substantially all, of the mold spores 21 are on the face 25 remote from the medium 13 and most of the mycelia extends through the sheet 17 and lies within the medium 13. During the growth process, the water of the mold suspension 15 is absorbed by the sheet 17 and to a lesser degree in the medium 13, and so in FIG. 2, the suspension 15 is not illustrated. The absorption of water by the sheet 17 allows the sheet to adhere to the medium 13.

After optimum growth of the mold has occurred, the sheet 17 and the mold colony 19 on the outer face 25 are removed from the medium 13 by peeling the sheet off of the medium. This can be accomplished manually with an appropriate tool, such as forceps. By peeling the sheet 17 from the medium 13, the spores 21 and the mycelia 23 on the face 25 are separated from the spores and mycelia on the face 27 and/or in the medium 13. As much of the mycelia lies within the medium 13 and/or on the face 27, the peeling step alone separates most of the spores from most of the mycelia 23. The peeling step should be carried out gently to avoid taking much, if any, of the medium with the sheet 17.

Next, the sheet 17 and the mold colony 19 thereon are dried under sterile conditions, such as in a sterile petri dish. Preferably, the drying is accomplished at ambient temperature and it may take from four to ten days.

The sheet 17 is then placed on a supporting surface 28 with the outer face 25 facing upwardly and the dried mold colony 19 is removed from the face 25. As shown in FIG. 4, this is preferably accomplished by scraping the mold colony 19 from the face 25 utilizing a knife 29 or other suitable implement. By scraping the mold colony 19 from the face 25, the mold spores 21 on the face 25 becomes separated from all of the mycelia 23, except the mycelia which are also on the face 25. The scraping step should be carried out gently to avoid scraping off much, if any, of the material of the sheet 17. The removed mold colony 19 immediately after scraping may be too moist for immediate sieving and should be dried for an additional period of time. For example, drying may be carried out at ambient temperature for two to four days. A desicator could be used to reduce the humidity of the air and promote drying of the removed mold.

Following drying, the removed mold spores 21 and mycelia 23 are sieved by a sieve 31 to separate at least major portions of the mold spores from the mycelia to thereby obtain the sieved mold spore material 32. The sieve 31 may be agitated as desired. The mold spores and mycelia may be sieved one or more times, and the sieve preferably has a U.S. Sieve Designation of 325 which has 0.0017 inch openings and a 0.0012 inch nominal wire diameter. The mold spores tend to pass through the sieve 31 and are collected in a clean container 33. Most of the mycelia and fragments of the sheet 17 tend to be retained on the sieve and do not pass through it. Preferably, the sieving operation is completely enclosed by mounting the sieve on an upper container 35 which is nested within the container 33 and which has its upper end closed by a lid 37.

The resulting mold spore material 32 contains mold spores and a small percentage of mycelia fragments. A purity of 90 to 95 percent of the mold spore material 32 is obtained utilizing the above-described process.

To reduce the likelihood of contamination of the mold, it should be handled and dried under sterile conditions. For example, all of the mold handling equipment is sterilized. In addition, the scraping and subsequent drying steps should be carried out in a laminar flow biological hood which materially reduces the contamination to which the mold would otherwise be subjected.

The mold spores of the mold material 32 are substantially unbroken, and accordingly, the surface antigens can be extracted from them. In a preferred method, a known weight of the mold spore material 32 is placed into a known volume of an extraction liquid and stirred gently while under reduced temperatures in a refrigerator utilizing a magnetic stirrer. For example, the temperature may be in the range of from about 4 to 6 degrees C. A standard known mold antigen extraction solution, such as a Coca's extraction solution, can be utilized. Because the mold spores have not been broken open and because the extraction step does not chemically breakdown the mold spores, essentially only the outer surfaces of the mold spores are exposed to the extraction solution and consequently, only the surface antigens are extracted.

EXAMPLE I

A suspension of Alternaria mold was innoculated directly onto a sterile petri dish containing Sabouraud's medium and overlaid with Whatman 54 filter paper. The mold was allowed to grow for fourteen days. After fourteen days, the filter paper was peeled off of the medium, transferred to a second sterile petri dish and air-dried at ambient temperature for seven days. The mold on the upper surface of the filter paper was then scraped off using a sterile knife and transferred to a sterile container. The scraped material was allowed to dry for seven days at ambient temperature and then sieved once through a sieve having a U.S. sieve designation of 325. The scraping and subsequent drying steps were carried out in a laminar flow biological hood. The material which passed through the sieve was put in suspension with a white cell counting solution and viewed microscopically in a cell counting chamber. On an average, there were 90-95 percent mold spores to 5-10 percent mycelia fragments.

EXAMPLE II

A suspension of Ulocladium mold was innoculated directly onto a sterile petri dish containing Murashige and Skoog medium and overlaid with #54 filter paper. The mold was allowed to grow for fourteen days. After fourteen days, the filter paper was peeled off of the medium, transferred to a second sterile petri dish and air-dried at ambient temperature for seven days. The mold on the upper surface of the filter paper was then scraped off using a sterile knife and transferred to a sterile container. The scraped material was allowed to dry for seven days at ambient temperature and then sieved once through a sieve having a U.S. sieve designation of 325. The scraping and subsequent drying steps were carried out in a laminar flow biological hood. The material which passed through the sieve was put in suspension with white cell counting fluid and viewed microscopically in a cell counting chamber. On an average, there were 90-95 percent mold spores to 5-10 percent mycelia fragments.

Although an exemplary embodiment of the invention has been shown and described, many changes, modifications and substitutions may be made by one having ordinary skill in the art without necessarily departing from the spirit and scope of this invention.

What is claimed is:

1. A method of obtaining mold spore material from a mold colony which includes mold spores and mycelia, said method comprising:
providing a porous barrier on a medium which supports growth of the mold colony;
growing a mold colony which includes mold spores and mycelia on the medium to provide the mold spores and mycelia on one side of the barrier which is remote from the medium and mycelia in the medium and on the other side of the barrier;
removing the barrier from the medium, said barrier having at least some of the mold spores and mycelia on said one side of the barrier;

drying the mold spores and mycelia which are on the removed barrier;

removing at least some of the mold spores and mycelia from said one side of the barrier whereby said step of removing, separates the removed mold spores and mycelia from the mycelia on said other side of said barrier; and separating the mold spores from at least major portions of the mycelia removed from the barrier to thereby obtain the mold spore material, said step of separating including sieving the mold spores and mycelia removed from the barrier.

2. A method as defined in claim 1 wherein said step of growing includes planting the mold colony on a surface of the medium and said step of providing includes placing the barrier on the planted mold colony.

3. A method as defined in claim 1 wherein said step of providing includes placing the barrier on the medium and said step of growing includes planting the mold colony on the side of the barrier remote from the medium.

4. A method as defined in claim 1 including drying the removed mold spores and mycelia prior to said step of separating and after the second mentioned step of removing.

5. A method as defined in claim 1 including extracting the surface antigens of the sieved mold spores.

6. A method as defined in claim 1 including mixing a known amount of the mold spore material with a known amount of an extraction liquid and maintaining the mixture at a temperature below ambient to extract the surface antigens of the sieved mold spores and minimize breakdown of the mold spore extract.

7. A method as defined in claim 1 wherein said barrier includes a flexible porous sheet and said first-mentioned step of removing includes peeling the flexible porous sheet from the medium.

8. A method as defined in claim 1 wherein said second-mentioned step of removing includes scraping at least some of the first group of mold spores and mycelia from the barrier.

9. A method as defined in claim 1 wherein the porous barrier is filter paper.

10. A method as defined in claim 9 wherein said step of removing includes mechanically removing the mold spores and mycelia from said one side of the barrier.

11. A method of obtaining mold spore material from a mold which produces both mold spores and mycelia, said method comprising:

providing a culture medium suitable for growing the mold;

supporting a flexible porous sheet on said medium;

inoculating the mold onto the flexible porous sheet or the medium, growing the inoculated mold to provide mold spores and mycelia on one side of the flexible porous sheet which is remote from the medium and mycelia in the medium and on the other side of the flexible porous sheet;

peeling the flexible porous sheet from the medium, said peeled sheet having at least some of said mold spores and mycelia on said one side of the sheet;

drying the mold spores and mycelia on said one side of the flexible porous sheet;

scraping at least some of the mold spores and mycelia from said one side of the flexible porous sheet whereby said steps of peeling and scraping, separate the scraped mold spores and mycelia from the mycelia on said other side of said sheet;

drying the separated mold spores and mycelia; and sieving the separated and dried mold spores and mycelia to substantially separate the mold spores from the mycelia thereby to produce a mold spore material having a substantial mold spore content.

12. A method as defined in claim 11 wherein at least one of said steps of drying is carried out at essentially ambient temperature.

13. A method as defined in claim 11 wherein said step of sieving includes providing a sieve having a U.S. sieve designation of 325 mesh and utilizing said sieve to separate the mold spores from at least the major portion of the mycelia in said step of sieving.

* * * * *